Feb. 2, 1937. E. A. McILHENNY Plant Pat. 231
CAMELLIA
Filed Aug. 7, 1936
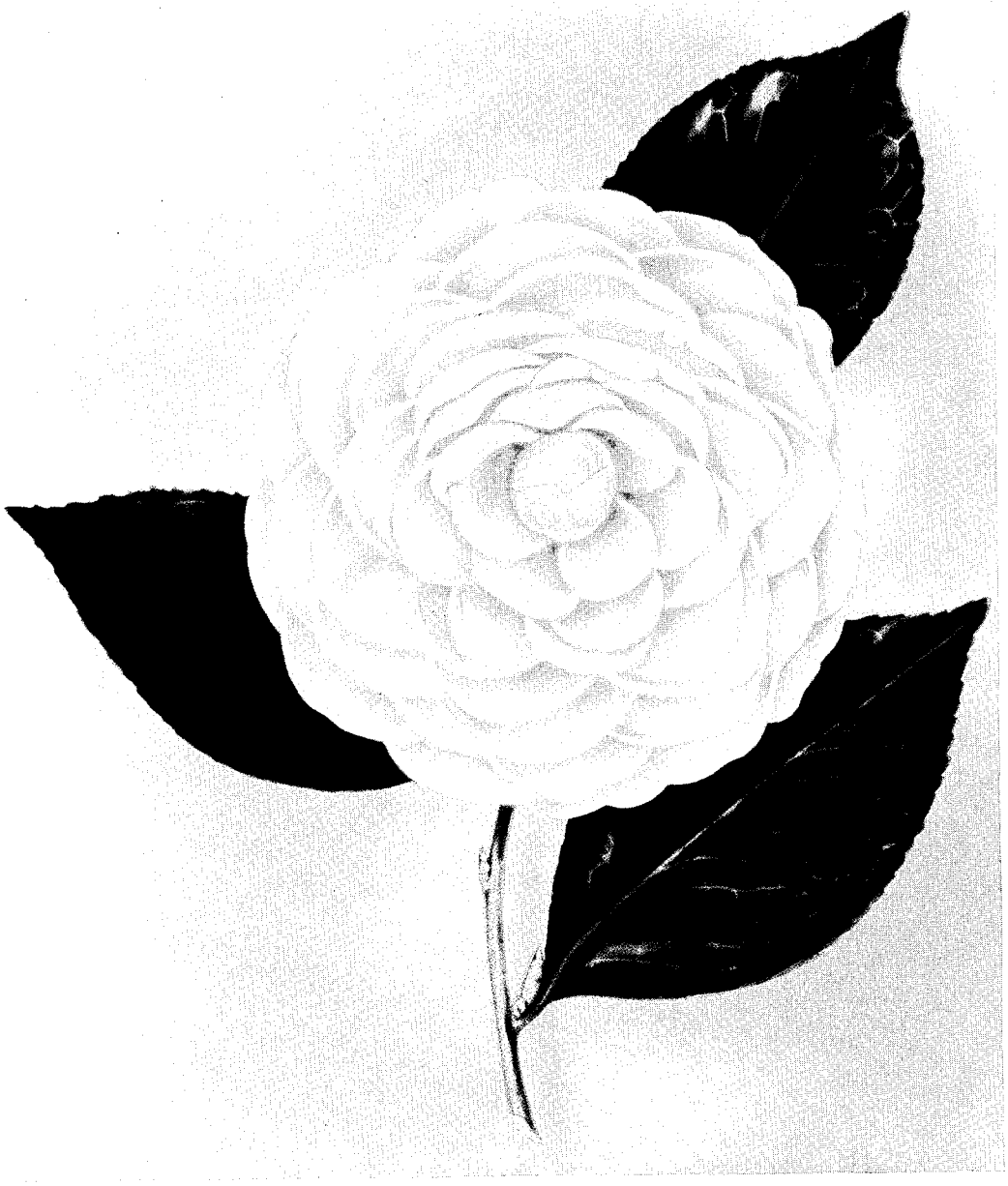
Inventor
E. A. McIlhenny
By Robb & Robb
Attorneys Patented Feb. 2, 1937

Plant Pat. 231

UNITED STATES PATENT OFFICE

231

CAMELLIA

Edward A. McIlhenny, Avery Island, La.

Application August 7, 1936, Serial No. 94,872

1 Claim. (Cl. 47—60)

The present invention relates to a new and distinct variety of *Camellia japonica*, a seedling of the known variety "Pink Perfection", developing a novelty in size and color of blossom.

More specifically, the features of this new shrub which characterizes its novelty reside in the brilliant flesh pink which, in the fully opened blossom, is so even and smooth that there is no variation in the color from the base of the petal to the tip. So far as I am aware, it is the only camellia that has this smooth uniform light pink color, combined with its outstanding size for a pink bloom, being double the size of the "Pink Perfection" referred to. The petals in the new variety, instead of being fully imbricated as in the "Pink Perfection", have a tendency to turn up at the outside tips giving the impression of a cupped petal. In the case of the "Pink Perfection" the petals are lighter toward the center and the coloring is therefore not uniform as in the new variety.

The foregoing characteristics have been found by asexual reproduction to be fixed.

The following is a detail description of this new variety, reference being made to Ridgway's color standard as regards color terminology:—

Parentage:
Seedling of Pink Perfection.

Classification:
Bontanic—*Camellia japonica.*

*Flower*

Blooming habit:
Blooms late—February 1st to March 15th.

Bud:
*Size.*—Medium.
*Form.*—Globular.
*Sepals.*—Smooth.
*Calyx.*—Large, smooth.

Bloom:
*Size.*—Large, 3¾'' to 4½'' when fully expanded.
*Borne.*—Singly.
*Stems.*—Strong.
*Form.*—When first opened—petals turn in, cupped. When fully opened—flat.
*Petalage.*—Fully imbricated, very double.—Stamens hidden. Number of petals about 72.
*Color.*—Geranium pink, uniform.

Petals:
*Texture.*—Thick, soft.
*Appearance.*—Inside satiny.
*Form.*—Round, notched.
*Arrangement.*—Imbricated.
*Fragrance.*—None.
*Lasting quality.*—On the plant—long. As cut flower—very long.

Genital organs:
Fully hidden by petals, immature.

Fruit:
None.

*Plant*

Form:
Shrub.

Growth:
Medium.
Upright, branching.

Foliage:
*Size.*—Medium.
*Quantity.*—Abundant.
*Color.*—New foliage—Van Dyke brown before the leaf breaks. Young leaves when two or three days old olive, veined dark green changing as leaves age to glossy bottle green. Old foliage—Light green, glossy. Under side duller.
*Shape.*—Lanceolate.
*Texture.*—Leathery, glossy, smooth. Underside smooth. Ribs and veins prominent.
*Edge.*—Serrated, large.

Wood:
*New wood.*—Color—Van Dyke brown. Bark—Smooth.
*Old wood.*—Color—Brown. Bark—Smooth.

I claim:
A new and distinct variety of *Camellia japonica*, characterized as to novelty by the uniform brilliant pink color and large size of its bloom, substantially as shown and described.

EDWARD A. McILHENNY.